United States Patent [19]

Dousa

[11] Patent Number: 4,806,532
[45] Date of Patent: Feb. 21, 1989

[54] INHIBITION OF EPITHELIAL PHOSPHATE TRANSPORT

[75] Inventor: Thomas P. Dousa, Rochester, Minn.

[73] Assignee: Mayo Foundation for Medical Education and Research, Rochester, Minn.

[21] Appl. No.: 785,485

[22] Filed: Oct. 8, 1985

[51] Int. Cl.$^4$ .......................... A61K 31/66; C12N 5/00
[52] U.S. Cl. .................................. 514/120; 435/240.1
[58] Field of Search ...................... 514/120; 435/240.1

[56] References Cited

U.S. PATENT DOCUMENTS

| | | | |
|---|---|---|---|
| 4,125,113 | 7/1980 | Eriksson et al. | 514/120 |
| 4,339,445 | 7/1982 | Eriksson et al. | 424/212 |
| 4,372,894 | 2/1983 | Helgstrand et al. | 260/941 |
| 4,386,081 | 5/1983 | Helgstrand et al. | 424/212 |
| 4,590,064 | 5/1986 | Gaffar | 424/49 |

OTHER PUBLICATIONS

Drach, J. C. and Shipman, C., (1977), Ann. N.Y., Acad. Sci., 284, 396–409.

Primary Examiner—Thomas G. Wiseman
Assistant Examiner—Charles L. Patterson, Jr.
Attorney, Agent, or Firm—Merchant, Gould, Smith, Edell, Welter & Schmidt

[57] ABSTRACT

Phosphonoformic acid, phosphonoacetic acid and the physiologically acceptable salts thereof are useful to inhibit the epithelial transport of phosphate anions in vivo and in vitro.

7 Claims, 2 Drawing Sheets

INHIBITION OF EPITHELIAL PHOSPHATE TRANSPORT

BACKGROUND OF THE INVENTION

This invention was made with the assistance of Grant No. AM-30759 awarded by the National Institute of Health. The Government has certain rights in this invention.

It has been established that phosphate (Pi) is reabsorbed from luminal fluid of renal proximal tubules via secondary active, $Na^+$-gradient [$Na^+$ extravesicular $>Na^+$ intravesicular; $na^+_o>$] dependent uptake across the microvillar brush border membrane (BBM). Numerous properties of this renal secondary active transport of Pi, namely functional changes in response to hormones, drugs and nutritional stimuli have been recently described, but the molecular structure of the Na-Pi cotransporter within renal BBM remains unknown. A similar $Na^+$-gradient dependent transport has been stablished in BBM of the epithelium of the small intestine.

The usefulness of compounds currently known to inhibit the $Na^+$-gradient-dependent Pi transport across BBM is rather limited. Arsenate ($AsO_2^{+2}$) competitively inhibits the BBM transport system for Pi, albeit with relatively low affinity. However, arsenate also interacts with and inhibits another component of BBM, alkaline phosphatase, and interferes with transepithelial Pi reabsorption by uncoupling oxidative mitochondrial respiration of proximal tubules. The inhibitory effect of arsenate on intermediary metabolism limits its use as specific blocker of BBM transport of Pi in studies on the intact cells, and prevents its use in vivo. Nicotinamide adenine dinucleotide (NAD) binds on BBM and inhibits competitively the $Na^+$- gradient dependent Pi uptakes in vitro. However, NAD also inhibits renal BBM-bound alkaline phosphatase and, after prolonged incubation with BBM in vitro, NAD is catabolized by NAD glycohydrolase and is hydrolyzed to adenosine, Pi and other components.

SUMMARY OF THE INVENTION

The present invention relates to a novel method of using known pharmacological agents. This method can be used in the treatment of conditions or symptoms due to certain pathological conditions in mammals. In particular, this invention relates to a method of inhibiting the transport of phosphate anions across epithelial membranes.

Thus, it has been found according to the present invention that phosphonic acids of the structural formula:

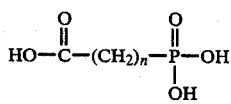

wherein n is 0 or 1, and physiologically acceptable salts thereof inhibit the epithelial transport of phosphate (Pi) and, hence the reabsorption of Pi in the kidney and in the intestine.

Thus, the present invention employs phosphonoacetic acid (PAA), phosphonoformic acid (PFA) or the salts thereof. A preferred compound for use in the present method, trisodium phosphonoformate (TPFA), is a potent inhibitor of Na-Pi cotransport across the luminal brush border membrane of renal proximal tubules and in the epithelium of the intestinal mucosa, i.e., in enterocytes. Its effects are reversible, specifc and trisodium phosphonoformate is nontoxic. Although the present method will be described primarily with respect to PFA and its salts, phosphonoacetic acid (PAA) and its physiological acceptable salts such as the di- and tri-sodium salts also exhibit substantial inhibition of Pi transport, and their use, either alone or in combination with PFA is also within the scope of this invention.

Thus, these inhibitors can be used to reduce the accumulation of phosphate in vivo. For example, they can be employed to treat secondary hyperparathyroidism in renal insufficiency. They can also increase the renal excretion of Pi and decrease the intestinal reabsorption of Pi. Possibly, the present compounds could be used even in the absence of renal function (in anephric patients) due to their ability to block intestinal reabsorption of Pi. They can also be used for the treatment of anamalous Pi retention in the syndrome of idopathic tumoral calcinosis, and as an adjunct treatment in primary hypoparathyroidism and pseudohypoparathyrodism, to prevent or diminish the retention of Pi and secondary calcifications.

PFA, PAA and their salts can also be employed in studies related to the Na-Pi transport system in vivo or in vitro. For example, they may provide the basis for the development of covalent affinity labels, to assist in the characterization of the Na-Pi cotransporter substance.

Therefore, the present invention is directed to a method of inhibition of the transport of phosphate across epithelial cell membranes by contacting the epithelial cells, either in vivo or in vitro, with an effective amount of photophonoformic acid, phosphonoacetic acid or the physiologically-acceptable salts thereof. Mixtures of these compounds may also be employed. This invention includes a method for decreasing the accumulation of excess phosphate in animals or in man, by the administrtion of PFA, PAA or the physiologically acceptable salts thereof to an animal or man in need of such treatment in an amount effective to reduce said accumulation.

the TPFA effect on BBMV uptake of $^{32}Pi$. The initial $Na^+$-dependent uptake of Pi and other solutes is denoted by open bars (▫), the uptake at equilibrium point (120 min) by shaded bars (▨). The initial uptake was measured at period of 20 sec for $^{32}Pi$ and at period of 15 sec for D-[$^3H$]-glucose and L-[$^3H$]-proline. The symbol (*) indicates a value significantly different from the control value (C) without TPFA (t-test).

Figure 3:
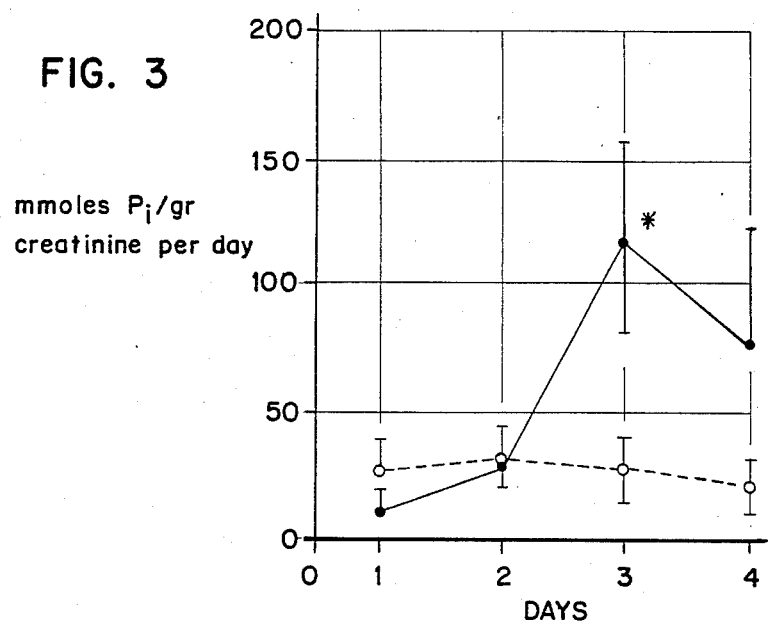

FIG. 3 is a graphic depiction of the effect of TPFA administration in vivo on urinary excretion of Pi in TPTX animals stabilized on low phosphate diet. Animals were injected i.p. on the beginning of day 2 and day 3 with TPFA (total daily dose was 500 mg TPFA/kg divided in 2 injections); controls received vehicle only. The Pi excretion per 24 hr is expressed relative to 24 hr excretion of creatinine. A solid line (● ●) denotes rats treated with TPFA (each point denotes means ±SEM; N=8); interrupted line (-- o -- o --) denotes control rats (N=9). The symbol (*) denotes values significantly increased compared to day 1 (P<0.025, by paired t-test; p <0.05, by group t-test).

Figure 4:
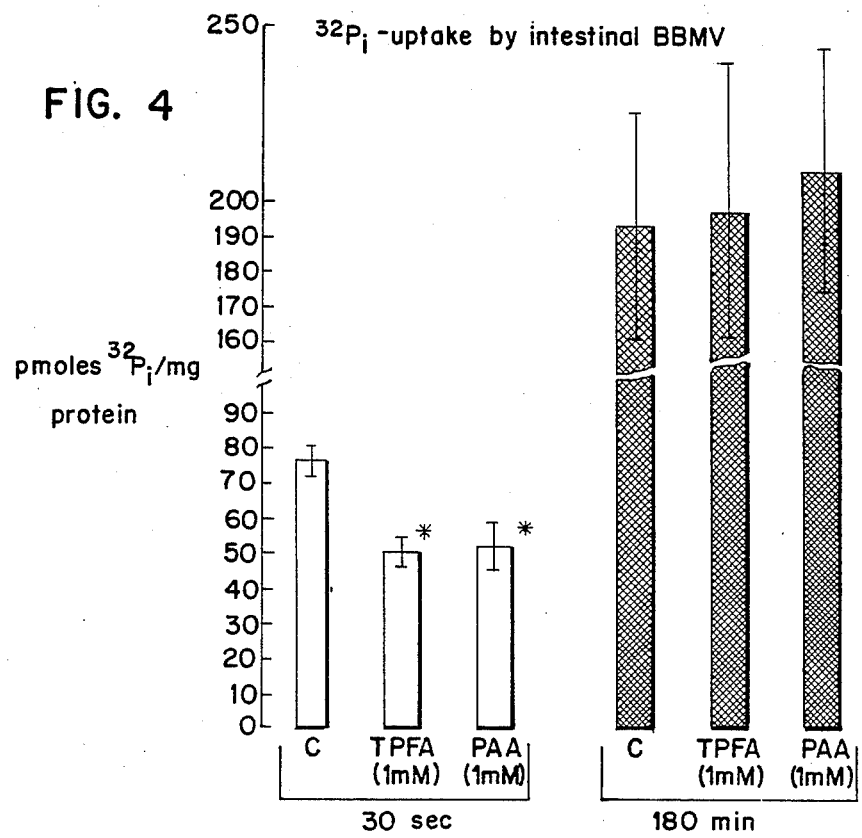

FIG. 4 is a graphic depiction of the effect of 1 mM TPFA and 1 mM PAA on Pi uptake by rat intestinal brush border membrane vesicles (BBMV) in the presence of Na$^+$-gradient [Na$_o^+$>Na$_i^+$] in vitro. The initial Na$^+$- dependent uptake of Pi (30 sec) is denoted by open bars ▫ (right side of the graph), the uptake at equilibrium point (180 min) by shaded bars ▨. The symbol (*) indicates values statistically significantly different from the control value (C) without addition of TPFA or PAA (t-test).

DETAILED DESCRIPTION FO THE INVENTION

The preparation of phosphonoformic acid and its physiologically acceptable salts and their use as antiviral agents is extensively described by B. F. H. Eriksson in U.S. Pat. No. 4,339,445, the disclosure of which is incorporated by reference herein.

Trisodium phosphonoformate (TPFA) and other phosphonocarboxylic acids and salts were examined for their effect on a N$^+$-gradient [Na$^+$ extravesicular >Na$^+$ intravesicular; Na$^+_o$>Na$^+_i$] uptake of phosphate (Pi) by renal cortical brush border membrane vesicles (BBMV). Both TPFA and to a lesser degree phosphonoacetic acid (PAA) inhibited in a dose-dependent manner the Na$^+$-gradient uptake of Pi by BBMV, but phosphonopropionic (PPA), hydroxymethylphosphonic, and phenylphosphonic acids were without effect. The inhibitory effect of TPFA was competitive, (Ki=4.6×10$^{-4}$M), reversible upon dilution, and specific only for the Na$^+$gradient-energized uptake of Pi. The Na$^+$-facilitated uptake of Pi by BBMV in the absence of a graident [Na$^+_o$=Na$^+_i$] was also inhibited. In contrast to Pi, the TPFA had no effect on Na$^+$-gradient-dependent uptake of L-[$^3$H]-proline and D-[$^3$H]-glucose, on diffusional uptake of $^{22}$Na$^+$, and it did not alter intravesicular voluem of BBMV. The relative (−Δ%) extent of inhibition by TPFA was not changed by increase or decrease in the pH and TPFA inhibited Pi uptake in the presence of a wide range (10–100 mM) of the Na$^+$gradient [Na$^+_o$>Na$^+_i$]. Inhibition of Pi transport by TPFA was analogous in BBMV prepared from kidneys of rats, mice, rabbits or dogs. Administration of TPFA (0.5 gm/kg per day) interperitoneally to thyroparathyroidectomized (TPTX) rats stabilized on low phosphate diet elicited an increase in urinary excretion of Pi, but did not change the excretion of Na$^+$, K$^+$ and calcium. The results show that TPFA and PAA are specific competitive inhibitors of the Na$^+$- Pi epithelial membrane cotransporter and are suitable probes for study of this transport system in mammalian kidney.

Moreover, the results showed that TPFA and PAA are inhibitors of Pi uptake by intestinal brush border membrane vesicles (BBMV) measured in the presence of Na$^+$-gradient [Na$^+$ extravesicular >Na$^+$ intravesicular; Na$_o^+$>Na$_1^+$], (FIG. 4).

Phosphonoformic acid may be formulated for use in human and veterinary medicine for therapeutic and prophylactic use, Since phosphonoformic acid is unstable in its free acid form and phosphonoacetic acid is corrosive, they are preferably used in the form of their physiologically acceptable salts, e.g., amine salts, e.g. dimethylamine and triethylamine salt, the ammonium salt, tetrabutylammonium salt, cyclohexylamine salt, cicyclohexylamine salt; and metal satls, e.g., mono-, di-and tri-sodium salt, mono-, di and tripotassium salts, magnesium salt, calcium salt and zinc salt.

Physiologically acceptable salts of phosphonoacetic acid and phosphonoformic acid are prepared by methods known in the art. Metal salts can be prepared by reacting a metal hydroxide with an alkylester of phosphonoformic acid or phosphonoacetic acid or with the free acid. Examples of metal salts which can be prepared in this way are salts containing Li, Na, K, Ca, Mg, Zn, Mn and Ba. A less soluble metal salt can be precipitated from a solution of a more soluble salt by addition of a suitable metal compound. Thus for examples, Zn, Mg and Mn salts of phosphonoformic acid can be prepared from phosphonoformic sodium salts. The metal ions of a metal salt of phosphonoformic acid can be exchanged by hydrogen ions, other metal ions, ammonium ion and ammonium ions substituted by one or more organic radicals by using a suitable cation exchanger.

In clincal practice, PFA, PAA or the salts thereof will normally be administered orally or by injection or infusion in the form of a pharmaceutical preparation comprising the active ingredient in combination with a pharmaceutically acceptable carrier which may be a solid, semisolid or liquid diluent or an ingestible capsule. The compound may also be used without carrier material. As examples of pharmaceutical preparations may be mentioned tablets, suspensions, liposomes, and the like. Usually the active substance will comprise between about 0.05 and 99%, or between 0.1 and 95% by weight of the preparation, for example between about 0.5 and 20% of preparations intended for injection and between about 0.1 and 50% of preparations intended for oral administration.

To produce pharmaceutical preparations in the form of unit dosages for oral application containing a compound of the invention, the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatin and also may include lubricants such as magnesium or calcium stearate or a Carbowax ® or other polyethylene glycol wax, and compressed to form tablets or cores for dragees. If dragees are required, the cores may be coated with concentrated sugar solutions which may contain gum arabic, talc and/or titanium dioxide, or alternatively with a film-forming agent dissolved in a volatile organic solvent or mixtures of organic solvents. Dyestuffs can be added to these coatings, for example, to distinguish between different contents of active substance. For the preparation of soft gelatin capsules consisting of gelatin and, for example, glycerol and a plasticizer, or similar closed capsules, the active substance may be admixed with a Carbowax ® or a suitable oil as e.g., sesame oil, olive oil, or arachis oil. Hard gelatin capsules may contain granules of the active substance with solid, pulverulent carries such as lactose, saccharose, sorbitol, mannitol (for example potato starch, corn starch or amylopectin), cellulose derivatives or gelatin, and may also include magnesium stearate or stearic acid as lubricants.

By suing several layers of the active drug, separated by slowly dissolving coatings sustained release tablets are obtained. Another way of preparing sustained release tablets is to divide the does of the active drug into granules with coatings of different thicknesses and compress the granules into tablets together with the carrier substance. The active substance can also be incorporated in slowly dissolving tablets made, for instance, of a fatty or waxy substance, such as a physiologically inert plastic.

In order to obtain unit dosages of oral preparations which are designed so as to prevent release of and possible decomposition of the active substance in the gastric juice, the tablets or capsules may be enteric-coated with a layer of a gastric juice-resistant enteric fluid or coating that is not dissolved at the acidic pH of the gastric juice. Thus, the active substance will not be released until the preparation reaches the intestine. As examples of such known enteric coatings maybe mentioned cellulose acetate phtalate, hydroxypropylmethylcellulose and phthalates.

Liquid preparations for oral application may be in the form of elixirs, syrups or suspensions, for example solutions containing from about 0.1% to 20% by weight of active substance, sugar and a mixture of ethanol, water, glycerol, propylene glycol and optionally aroma, sugar and/or dispersing agents.

The dosage at which the active ingredients are administered may vary within a wide range and will depend on various factors such as for example the severity of the condition, the age and wight of the patient, etc., and may have to be individually adjusted. As a possible range for the amount of PFA, PAA or a salt thereof which may be administered per kg per day may be mentioned from about 0.1 mg to about 2000 mg or from about 1 mg to about 1500 mg; or preferably from 50 mg to about 2000 mg or from 100 to about 1000 mg for oral administration, and from 10 mg to about 2000 mg or from 50 to about 500 mg for injection. In severe cases it may be necessary to increase these doses 5-fold to 10-fold or more. In less severe cases it may be sufficient to use up to about 500–1000 mg.

The pharmaceutical compositions containing the active ingredient may be formulated so that they provide doswes within these ranges either as a single unit dosage or as a multiple unit dosage.

The invention will be further described by reference to the following examples relating to the activity of TPFA and PAA.

MATERIALS AND METHODS

In vitro studies

The brush border membrane vesicles (BBMV) were prepared from renal cortical tissue of adult male Sprague-Dawley rats of an average body weight of about 220 grams. Rats were fed ad libitum standard rat chow containing 0.7% Pi and had free access to distilled water. Rats were sacrificed under anesthesia and dissected renal cortical tissue was used for preparation of BBMV fraction by the divalent cation-precipitation procedure, employed and described in detail in J. Clin. Invest., 67, 1347 (1981) and J. Biol. Chem., 258, 5695 (1983), with the following modifications: (a) $MgCl_2$ instead of $CaCl_2$ was added to crude homogenate (final concentration 10 mM $MgCl_2$) to precipitate membranes other than BBMV; (b) in the final step, BBMV were washed and equilibrated in a medium of pH=7.5, instead of pH=8.5. The enrichment and specific activities of typical BBM enzymes alkaline phosphatase (APases), γ-glutyamyl transferase (γ-GTT), leucineaminopeptidase (LAP) and maltase with use of these modifications were similar as in BBMV fractions prepared in our previous studies. As a final step in the preparative procedure, the BBMV fraction was washed and resuspended in a medium containing 300 mM mannitol and 5 mM Tris-HEPES adjusted to pH=t.5, referred to as "MTH-medium," unless specified otherwise. The analogous BBMV fractions, using the same procedure, were prepared from renal cortices of mongrel dogs, albino mice and New Zealand albino rabbits.

The BBMV uptake of $^{32}Pi$, D-[$^3$H]-glucose, L-[$^3$H]-proline and $^{22}Na^+$ was measured by means of a rapid filtration technique, as described in J. Clin. Invest., 67, 1347 (1981) and Am. J. Physiol., 246, F133–F139 (1984). Also, unless specified otherwise, the medium for the solute uptake assay consisted of following compounds (in final concentrations): 100 mM mannitol, 100 mM NaCl (or 100 mM KCl) and 5 mM Tris-HEPES (pH=7.5) and eitehr 0.1 mM $K_2H^{32}PO_4$, or 0.05 mM D-[$^3$H]-glucose, or 0.025 mM L-[$^3$H]-proline. IN the $^{22}Na^+$ uptake studies, the assay medium contained 100 mM $^{22}NaCl$ ($^{22}NaCl$ about $4\times10^{-5}$ cpm per tube), 100 mM mannitol and 5 mM Tris-HEPES (pH 7.5).

The uptake of $^{32}Pi$ in the presence of $Na^+$ gradient $[Na^+_o > Na^+_i]$, or in the absence of $Na^+$ (100 mM NaCl in the medium replaced by 100 mM KCl) showed a typical time-course with equilibration achieved at 120 min. In most experiments, the $Na^+$-gradient-dependent $^{32}Pi$ uptake in the concentrative "uphill" phase was measured at 20 seconds period. Since $Na^+$-independent Pi uptake in this time period was quantitatively minor component (<5%) of the $Na^+$-gradient-dependent Pi uptake, it was not routinely subtracted.

The reversibility of the inhibition of $^{32}Pi$ transport across BBMV by TPFA was explored using the following protocol. Freshly prepared BBMV fraction (0.68 mg protein/tube) was suspended either in solution containing 4 mM TPFA in MTH-medium, or the control aliquot in the MTH-medium without TPFA. The suspensions of BBMV were incubated for 10 min at room temperature. At the end of incubation period, incubation mixtures were diluted with 10 ml of ice-cold MTH-medium, resuspended and centrifuged at 35,000×g for 20 min. The supernatant was discarded and BBMV pellet was suspended in MTH-medium and then assayed for $Na^+$-gradient-dependent $^{32}Pi$ uptake.

The intestinal BBMV fractions were prepared from mucosa of rat small intestine of rats using the modified magnesium- precipitation method as described by B. Steiger and H. Murer [Eur. J. Biochem., 135, 95 (1983)]. This intestinal BBMV fraction is analogous to the BBMV fraction isolated from kidney. The uptake of $^{32}Pi$ in the presence of $Na^+$-gradient $[Na_o^+ > Na_i^+]$ was determined by a rapid filtration technique similar to that employed in the transport measurements on renal BBMV. The $Na^+$-gradient $[Na_o^+ > Na_i^+]$-dependent Pi uptake in the initial phase was measured after 30 sec. The $^{32}Pi$ uptake at equilibrium was measured at 180 min.

In vivo studies

Surgically thyroparathyroidectomized (TPTX) rats of 180–220 g body wt (Johnson Laboratories, Chicago, IL) were placed in metabolic cages and were fed 15 g of the low phosphate (P =0.07%) diet (ICN, Cleveland, OH) and 25 ml distilled water per day prior to and throughout the study (J. Clin. Invest. 67, 1347 (1981)).

The animals were weighed daily. Urine samples (24-hour period) were collected each day for determination of urine volue, creatinine, Pi, $Ca^{++}$, $Na^+$ and $K^+$. After stabilization of rats on the low phosphate diet for 4 days, the "experimental" group of rats were injected with TPFA (500 mg/kg b wt) intraperitoneally, divided in two daily doses, while the "control" rats received the vehicle only. TPFA for i.p. injection was dissolved in distilled water and the control animals were injected with the same volume of NaCl solution containing the equimolar amount of $Na^+$. When appropriate, the results were evaluated statistically using student's t-test for either group or paired comparisons. Values of P >0.05 were considered nonsignificant (NS).

Materials

Phosphonoformic acid, trisodium salt hexahydrate (TPFA), phosphonoacetic acid (PAA), phosphonopropionic acid (PPA) and the other alkylphosphonic and arylphosphonic acid derivatives as well as phosphoesteric compounds were purchased from either Sigma Co., St. Louis, Mo., Aldrich Co., Milwaukee, Wis. or Alpha Co., Danvers, Mass. Methylenediphosphonic acid was purchased from Sigma Co., St. Louis, Mo., and disodium ethane-1-hydroxy-1,1-diphosphonate (EHDP) was obtained from Procter and Gamble Co., Cincinnati, OH. Radioisotopes $^{32}Pi$, L-[$^3H$]-proline, D-[$^3H$]-glucose and $^{22}Na^+$ were purchased from New England Nuclear Co. (Boston, Mass.). ATP, ouabain and all other chemicals and biochemicals, all of the highest purity grades, were purchased from the standard suppliers.

RESULTS

In vitro studies of BBM transport

Compounds studied in the present experiments which inhibited BBM transport of Pi without hydrolysis to release more than 5% Pi are listed in Table 1.

TABLE 1

Effects of phosphono-compounds on $Na^+$-gradient [$Na_o^+ > Na_i^+$]-dependent uptake of $^{32}Pi$ by BBMV prepared from rat kidney cortex.

| | N | Δ%* | [Conc.]** | Note |
|---|---|---|---|---|
| 1. Trisodium Phosphonoformate (TPFA) | (5) | −53% | (1 mM) | no hydrolysis |
| 2. Phosphonoacetic Acid (PAA) | (5) | −18% | (1 mM) | no hydrolysis |
| 3. Disodium Ethane-1-hydroxyl, 1-diphosphonate (EHDP) | (3) | −27% | (1 mM) | no hydrolysis |
| 4. Methylene diphosphonic Acid (MDP) | (3) | −21% | (5 mM) | — |

*Inhibition expressed as percent decrease from control value.
**Concentration tested. The initial uptake in the presence of $Na^+$-gradient [$Na_o^+ > Na_i^+$] was measured at 20 sec period of the uphill concentrative uptake. Assays were done in duplicate or triplicate. N denotes number of experiments.

Of the compounds which decreased the $Na^+$ gradient dependent uptake of Pi by BBMV, the most potent inhibitor, on an equimolar basis, was trisodium phosphonoformate (TPFA). The effect of TPFA and phosphonoacetic acid (PAA) on the Pi uptake is summarized on Table 2.

TABLE 2

| | TPFA $^{32}Pi$ Uptake* | | | PAA $^{32}Pi$ Uptake* | | |
|---|---|---|---|---|---|---|
| Additions | 20 sec | 120 min | Δ% ratio[b] | 20 sec | 120 min | Δ% ratio[b] |
| 0 (control) | 1070 ± 66[a] | 246 ± 45 | +373 ± 57 | 1163 ± 134[a] | 275 ± 49 | +377 ± 91 |
| 0.2 mM | 869 ± 45[c] | 264 ± 53 | +262 ± 44[c] | 1057 ± 89 | 320 ± 80 | +305 ± 101 |
| 1.0 mM | 541 ± 39[c] | 248 ± 47 | +137 ± 27[c] | 1019 ± 94 | 274 ± 51[c] | +331 ± 86 |
| 5.0 mM | 153 ± 28[c] | 239 ± 44 | <0.0 | 876 ± 68 | 269 ± 52[c] | +261 ± 78[c] |

*The BBMV were incubated with TPFA or with PAA for 5 min. prior to the onset of $^{32}Pi$ uptake measurements. The $^{32}Pi$ uptake, measured in the presence of $Na^+$-gradient [$Na_o^+ > Na_i^+$], is expressed in pmoles/mg protein.
[a]Mean ± SE of 3–5 experiments.
[b]ratio of $Na^+$-gradient-dependent uptake at uphill phase (20 sec) and late (120 min.) "equilibrium phase" of $^{32}Pi$ transport.
[c]Values significantly different from controls by paired t-test.

The data summarized on Table 2 indicate that TPFA and PAA inhibit the $Na^+$-gradient-dependent BBMV uptake of Pi in a dose-dependent manner.

Figure 1:
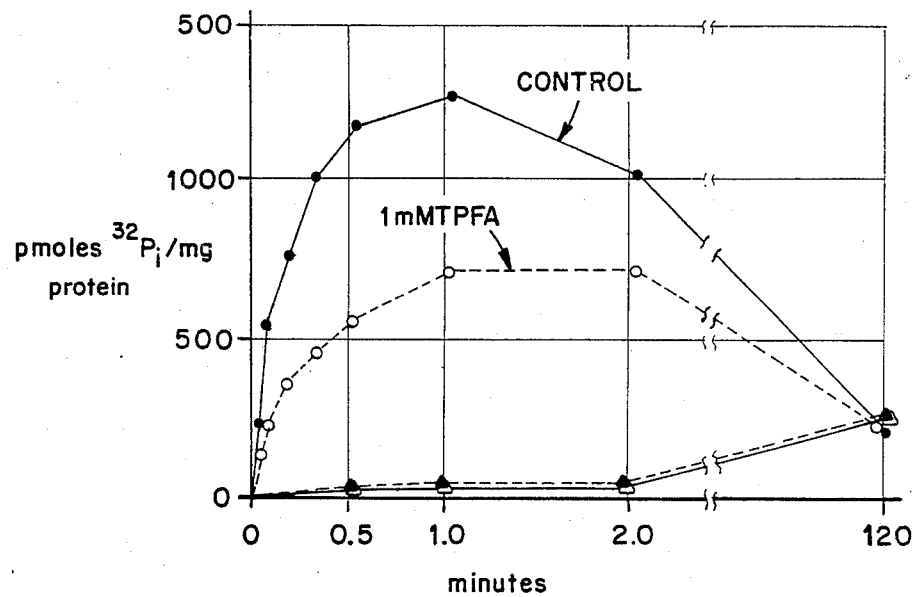
FIG. 1 is a graphical depiction of the time course of the $^{32}Pi$ uptake by renal brush border membrane vesicles (BBMV) in presence of $Na^+$-gradient [$Na^+_o >Na^+_i$] without (control—●—●—) or with 1 mM TPFA (--O--), and of $Na^+$-independent $^{32}Pi$ uptake (NaCl replaced by KCl in the medium) with (—▲—) or with (—Δ—) 1 mM TPFA.

The actions of TPFA, the most potent inhibitor, on BBM transport properties and on BBm enzyme activities were studied in greater detail. Addition of TPFA decreased the rate of the $^{32}Pi$ uptake in the initial "uphill" phase (2–30 seconds), uptake at the peak (60 seconds), but did not influence the uptake of $^{32}Pi$ after equilibration at 120 min as shown by FIG. 1. TPFA had similar inhibitory effect regardless whether in the $Na^+$-gradient [$Na^+_o > Na^+_i$], the $Na^+$ in the outer medium was accompanied by $Cl^-$ (FIG. 1), or by $SCN^{-as}$ an anion (data not shown). In the absence of $Na^+$ (NaCl replaced by KCl), TPFA had no effect on the $^{32}Pi$ uptake by BBMv (FIG. 1). In BBMV preequilibrated with $Na^+$[$Na^+_o=Na^+_i$] the uptake of $^{32}Pi$ was more than 100% higher than in the presence of $K^+$[$K^+_o=K^+_i$]. When tested under $Na^+$ equilibrium conditions [$Na^+_i=Na^+_o$], TPFA inhibited the $^{32}Pi$ uptake in the initial fast uptake phase (0–60 seconds). On the other hand, the $^{32}Pi$ uptake at 120 min, or the $^{32}Pi$ uptake when NaSCN was replaced by equimolar KSCN [$K^+_o=K^+_i$] was not influenced by TPFA (data not shown).

The reversibility of the inhibitory effect of TPFA on $Na^+$-gradient-dependent Pi transport was also examined. The BBMV suspension was first preincubated with TPFA, then diluted in TPFA-free MTH-medium. The $^{32}Pi$ uptake was then measured in washed BBMV. After washout of TPFA by dilution, the rate $Na^+$-gradient-dependent BBMV uptake of Pi was indistinguishable from control BBMV, not exposed to TPFA. The results of this study are summarized in Table 3.

TABLE 3

The Na$^+$-gradient [Na$_o^+$ > Na$_i^+$]-dependent $^{32}$Pi uptake of BBMV with and without previous exposure to TPFA. Fraction of BBMV was incubated in a medium (300 mM mannitol, 5 mM Tris-HEPES; pH = 7.5) either without (controls), or with 5 mM TPFA at the room temperature for 10 min. At the end of incubation, BBMV were diluted 1:10 in isotonic buffered mannitol, collected by centrifugation and assayed for Na$^+$-gradient dependent $^{32}$Pi uptake.

| | $^{32}$Pi uptake (pmoles/mg protein) | | | | | |
|---|---|---|---|---|---|---|
| | Controls | | | TPFA-preincubated | | |
| Experiment No. | 20 sec | 120 min | Δ%** | 20 sec | 120 min | Δ%** |
| 1 | 983 ± 27* | 256 ± 20 | +283 | 1240 ± 25 | 326 ± 5 | +280 |
| 2 | 1008 ± 10 | 220 ± 5 | +358 | 1128 ± 38 | 293 ± 3 | +371 |

*Denotes mean ± SEM of replicate samples
**Ratio of the Na$^+$-gradient-dependent $^{32}$Pi uptake at uphill (20 sec) and late equilibrium (120 min) phase of $^{32}$Pi transport.

Figure 2:
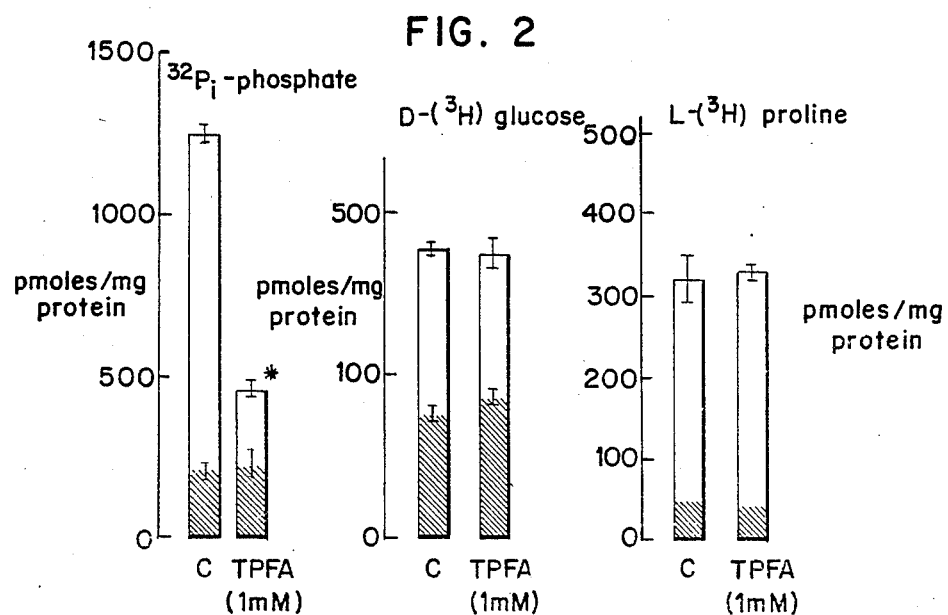

To explore the specificity of TPFA effects on Pi transport system, the actions of this compound on Na$^+$-gradient [Na$^+_o$>Na$^+_i$] dependent uptake of L-[$^3$H]-proline and D-[$^3$H]-glucose by BBMV were determined. In contrast to inhibition of Na$^+$-gradient-dependent uptake of Pi, PFA had no inhibitory effect on Na$^+$-gradient-dependent uptake of L-[$^3$H]-proline or of D-[$^3$H]-glucose (FIG. 2). The equilibrium uptake of L-[$^3$H]-proline at 120 minutes (expressed in pmoles/mg protein; means ± SEM) in the presence of 1 mM TPFA (43+1; n=4) was not different from controls (43±3; n =4). Also, the uptake of D-[$^3$H]-glucose at 120 minutes (pmoles/mg protein; mean ± SEM) in control BBMV (66±15; n =3) was not altered in the presence of 1 mM TPFA (65±12; n=4).

The diffusional uptake of $^{22}$Na$^+$ by BBMV [Na$^+_o$>Na$^+_i$] was also not influenced by added TPFA either in the initial phase (20 sec), or after 120 min equilibration. The results of this study are summarized in Table 4.

TABLE 4

| | $^{22}$Na$^+$ uptake (nmoles/mg protein)* | |
|---|---|---|
| | 20 sec | 120 min |
| Controls (no additions) | 42 ± 4* | 166 ± 25 |
| 1 mM PFA | 45 ± 3 | 192 ± 30 |

*Mean ± SEM of 3 experiments, each measured in replicate samples. The uptake in the initial phase (20 sec) and at equilibrium (120 min) was not significantly different.

Finally, we compared the TPFA effect on Na$^+$-gradient [Na$^+_o$>Na$^+_i$] dependent Pi transport across renal BBMV from the four mammalian species. The results of this study are summaried in Table 5.

TABLE 5

Effects of TPFA on Na$^+$-gradient [Na$_o^+$ > Na$_i^+$] dependent uptake of $^{32}$Pi by BBMV from kidneys of rat, mouse, rabbit and dog. The $^{32}$Pi uptake is expressed in pmoles Pi/mg protein/time.

| Additions | 20 sec | 120 min | Additions | 20 sec | 120 min |
|---|---|---|---|---|---|
| | Rat $^{32}$Pi-uptake | | | Mouse $^{32}$Pi-uptake | |
| Control | 1570 ± 31* | 361 ± 9 | Control | 824 ± 9 | 368 ± 7 |
| 1 mM TPFA | 783 ± 6 (−59.1%)** | 359 ± 8 | 1 mM TPFA | 299 ± 8 (−63.7%) | 390 ± 74 |
| 5 mM TPFA | 344 ± 7 (−78.0%) | 379 ± 34 | 5 mM TPFA | 97 ± 7 (−88.2%) | 404 ± 12 |
| | Dog $^{32}$Pi-uptake | | | Rabbit $^{32}$Pi-uptake | |
| Control | 1178 ± 15 | 410 ± 5 | Control | 768 ± 7 | 551 ± 15 |
| 1 mM TPFA | 476 ± 9 (−59.6%)** | 377 ± 6 | 1 mM TPFA | 279 ± 4 (−63.7%) | 532 ± 19 |
| 5 mM TPFA | 110 ± 3 (−90.7%) | 428 ± 9 | 5 mM TPFA | 107 ± 5 (−86.1%) | 549 ± 11 |

*Mean ± SEM of replicate samples
**In parentheses: percent decrease relative to control value (no additions)

In concentrations 1 mM and 5 mM the added TPFA proportionally inhibited the uphill Na$^+$-gradient-dependent Pi uptake by BBMV from rat, mouse, canine and rabbit kidney. The relative (−Δ%) inhibition tended to be even more pronounced in species other than rat. The uptake of $^{32}$Pi at 120 min equilibrium was not diminished by TPFA.

In vivo studies

The effect of TPFA on renal excretion of Pi in vivo was examined in TPTX rats stabilized on low phosphate diet, a homeostatic state of maximum proximal tubular reabsorption of Pi. The urinary excretion of Pi and other electrolytes was expressed relative to the quantum of excreted creatinine, an approximate measure of the glomerular filtration rate (GFR) See, R.E. espinosa et al., Am. Journal of Physiol., 246, F133 (1984). Administration of TPFA intraperitoneally, in two daily doses, elicited severalfold increase in urinary excretion of Pi phosphate as shown in FIG. 3. In contrast to the increase in Pi excretion, rats injected with TPFA did not change urinary excretion of Na$^+$, K$^+$ or calcium, measured in the same samples of the urine. The results of this study are summarized on Table 6.

TABLE 6

Effect of in vivo administration of TPFA on the urinary excretion of Pi and other electrolytes in thyroparathyroidectomized (TPTX) rats.

| Parameter | | Day 1 | Day 2 | Day 3 | Day 4 |
|---|---|---|---|---|---|
| Phosphate excretion | Control: | 25.3 ± 13.9* | 28.2 ± 17.3 | 28.7 ± 14.1 | 23.9 ± 10.8 |
| | Experimental: | 11.8 ± 6.0 | 30.8 ± 6.6 | 122.1 ± 37.8** | 79.8 ± 46.9 |
| Sodium excretion | Control: | 18.9 ± 8.0 | 22.8 ± 10.0 | 24.7 ± 11.1 | 22.0 ± 8.7 |
| (mmoles/mg creatinine) | Experimental: | 6.8 ± 1.1 | 8.0 ± 1.1 | 19.4 ± 11.6 | 15.1 ± 7.0 |
| Potassium excretion | Control: | 20.3 ± 8.6 | 23.8 ± 10.5 | 26.4 ± 12.0 | 23.9 ± 10.0 |
| (mmoles/mg creatinine) | Experimental: | 7.3 ± 1.0 | 7.6 ± 1.1 | 11.8 ± 3.9 | 12.9 ± 5.3 |
| Calcium excretion | Control: | 0.33 ± 0.15 | 0.5 ± 0.21 | 0.43 ± 0.16 | 0.46 ± 0.19 |
| (mmoles/mg creatinine) | Experimental: | 0.3 ± 0.07 | 0.2 ± 0.09 | 0.3 ± 0.2 | 0.6 ± 0.5 |

*Mean ± SEM of 8-9 rats
**Significantly increased, compared to Day 1 (P < 0.025; paired t-test)

in vitro studies on Pi transport across intestinal BBMV.

The effect of TPFA and PAA on the uptake of Pi and other solutes by intestinal BBMV in the presence of $Na^+$-gradient $[Na_o^+ > Na_i^+]$ both in the initial phase of uptake and at equilibrium was also determined.

TABLE 7

Effect of 1 mM TPFA and 1 mM PAA upon $Na^+$-gradient $[Na_o^+ > Na_i^+]$-dependent uptake of solutes by BBMV from rat small intestine. The uptakes in the initial phase (15 or 30 sec) and equilibrium phase (180 or 120 min) are expressed in pmoles/mg of BBMV protein.

| | $^{32}$Pi-phosphate uptake (pmoles/mg protein) | | | L-[$^3$H]—proline uptake (pmoles/mg protein) | |
|---|---|---|---|---|---|
| | 30 sec | 180 min | | 15 sec | 120 min |
| control | 75 ± 3* | 151 ± 4 | control | 27 ± 0.2 | 53 ± 2 |
| 1 mM TPFA | 44 ± 2** | 146 ± 5 | 1 mM TPFA | 27 ± 0.4 | 54 ± 0.1 |
| 1 mM PAA | 51 ± 0.3** | 163 ± 6 | 1 mM PAA | 27 ± 1.0 | 55 ± 1.0 |

| | D-[$^3$H]—glucose uptake (pmoles/mg protein) | | | $^{14}$C—succinate uptake (pmol/mg protein) | |
|---|---|---|---|---|---|
| | 15 sec | 120 min | | 15 sec | 120 min |
| control | 67 ± 0.5 | 57 ± 2 | control | 118 ± 7 | 78 ± 3 |
| 1 mM TPFA | 69 ± 2 | 57 ± 2 | 1 mM TPFA | 125 ± 3 | 81 ± 1 |
| 1 mM PAA | 68 ± 3 | 61 ± 3 | 1 mM PAA | 127 ± 2 | 89 ± 3 |

*Mean ± SEM of replicate samples
**Significantly lower than corresponding control value (P < 0.005, t-test)

Both TPFA and PAA at 1 mM concentrations markedly inhibited the initial $^{32}$P uptake, but did not effect the uptake of Pi at equilibrium (FIG. 4, Table 7). The inhibitory effect of TPFA and PAA is specific for Pi compared to the uptakes measured for the other solutes tested (Table 7). While both TPFA and PAA caused a marked inhibition of the initial Pi uptake, at the same concentrations these compounds had no effect on the initial or on the equilibrium uptakes of L-proline, D-glucose and succinate (Table 7).

DISCUSSION

The results of these experiments indicate the TPFA and PAA can act as specific, reversible and competitive inhibitors of the $Na^+$-gradient-dependent BBM renal transport of Pi.

It is of interest to consider the structural requirements of organic compounds, which are derivatives of phosphonic acid, for their interaction with the $Na^+$-Pi cotransporter in BBM and with other components of BBM. Certain phosphonocarboxylic acids and their salts, in particular TPFA, seem to posses suitable properties to inhibit Na-Pi cotransport. Comparison of the inhibitory effects TPFA, PAA and phosphonopropionic acid (inactive) suggest that closeness of proximity of carboxylic group to phosphonyl radical is of major importance. The requirement of a carboxylate group—a negatively charged component --in juxtaposition to phosphonate moiety is also supported by the observation that the sodium salts of hydroxymethylphosphonic acid, phenylphosphonic acid, and 2-aminoethylphosphonic acid all lacked the inhibitory effect. Free, disscíable groups in the molecule of TPFA and PAA are apparently needed for the inhibition, since the trimethylesters of TPFA and PAA were also without inhibitory effort.

The inhibition of Pi uptake by TPFA is not due to diminishing of the driving force for Pi uptake, the $Na^+$-gradient $[Na^+_o > Na^+_i]$. Firstly, TPFA did not inhibit other Na-gradient-dependent transport systems, the BBM transport of D-[3H]-glucose of L-[$^3$H]-proline (FIG. 2). TPFA did not alter rate of $Na^+$ permeability of BBM and hence the rate of dissipation of $[Na^+_o >$-$Na^+_i]$ gradient (Table 4). The inhibitory effect of TPFA was observed to persist even when the steepness of $Na^+$ gradient $[Na^+_o > Na^+_i]$ is markedly reduced. Further, the Pi uptake by BBM is not inhibited by TPFA when NaCl is replaced by KCl in the medium (FIG. 1). Finally, PFA inhibits Pi transport across BBM even in the absence of $Na^+$-gradient, $[Na^+_o > Na^+_i]$ which suggest that it interacts directly with Na-Pi cotransporter.

Our experiments on unanesthetized rats (FIG. 3) provide at least preliminary indication that TPFA can inhibit renal tubular Pi transport in vivo, since PFA increases specifically the urinary excretion of Pi, but not of other solutes (Table 6). The most plausible explanation for this in vivo finding is that TPFA inhibited proximal tubular Pi reabsorption at the luminal BBM uptake step. The design of the in vivo experiments, namely the use of TPTX animal, provides evidence that TPFA does not influence the Pi excretion indirectly by changing the secretion or action of hormones which are known to regulate the proximal renal tubular Pi reabsorption at the luminal BBM uptake step; namely parathyroid hormone, calcitonin, or thyroid hormones.

The specificity, reversibility and competitive nature of the TPFA inhibition of Pi transport suggest that the $Na^+$-Pi cotransporter can be examined without encountering TPFA interference with other transport systems in BBM. Unlike some other inhibitors of Pi transport known to date, namely EHDP and arsenate, the TPFA is without inhibitory effect on other membrane components, such as the BBM enzymes APase, and BaLM enzyme (Na-K)ATPase (data not shown). TPFA is a relatively non-toxic compound, is taken up by intact cells, and interferes with basic cellular functions reversibly and only in relatively high concentrations. The antiviral actions of TPFA are most likely due to inhibition of several viral-specific DNA and RNA polymerases and of two nucleases. Inhibitory TPFA actions on these viral-specific enzymes are virtually all noncompetitive or uncompetitive, suggesting a mechanism of action different from this newly found competitive inhibition of $Na^+$-Pi-cotransport.

Similarly, as in renal cortical BBMV, TPFA and PAA inhibited the initial Pi uptake in the presence of $Na^+$-gradient $[Na_o^+ > Na_i^+]$ in the intestinal BBMV. Also, in the intestinal BBMV, the inhibition specificity was confirmed by comparison with the other transport systems (Table 7). Unlike Pi uptake, the uptakes of L-proline, of succinate and the uptake of D-glucose were not inhibited. As in renal BBMV, neither TPFA or PAA inhibited intestinal BBM alkaline phosphatase (data not shown).

TPFA does not undergo biotransformation and general toxicity studies showed not toxic effects on bone. On the other hand, EDHP blocks 1-α-hydroxylation of 25-OH-vitamin-D as well as the bone mineralization process. Arsenate, in concentrations even lower than those needed to inhibit the BBM uptake of Pi, is toxic to cellular metabolism, mainly to mitochondrial respiration. Although it cannot be excluded that TPFA or PAA may have some yet unknown biochemical and biologic effects which are unrelated to the inhibition of BBM cotransport of Na-Pi, these compounds appear to be more specific and far less toxic than any other inhibitors of Na-Pi cotransport known to date. Furthermore, the observation that TPFA and PAA neither interfere with, nor are detected in, standard assays for Pi indicates a major advantage for use of these compounds in studies of Pi processing in vivo. The inhibition of $Na^+$-gradient-dependent renal BBM transport of Pi is not unique for rat, but was observed in all examined experimental animal species (Table 5).

Finally, a potentially important feature of TPFA and PAA is that these compounds are not simple inorganic anions such as arsenate. Therefore, structural modifications could provide a suitable basis for development of derivatives which can act as irreversible inhibitors of the $Na^+$-Pi cotransporter in BBM and yield affinity-labeling probes specific for this important transport system.

The invention has been described with respect to various specific and preferred embodiments. However, it should be understood that many variations or modifications may be made while remaining within the spirit and scope of the invention.

What is claimed is:

1. A method of decreasing the accumulation of phosphate in an animal or man comprising administering to an animal or man in need of such treatment an effective amount of a compound of the formula;

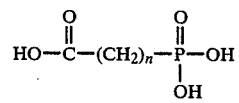

wherein n is 0 or 1, or a physiologically acceptable salt thereof.

2. The method of claim 1 wherein n is 0.

3. The method of claim 2 wherein the compound is a trialkali metal salt of phosphonoformic acid.

4. The method of claim 3 wherein the compound is trisodium phosphonoformate.

5. The method of claim 1 wherein n is 1.

6. The method of claim 5 wherein the compound is phosphonoacetic acid.

7. The method of claim 5 wherein the compound is trisodium phosphonoacetate or disodium phosphonoacetate.

* * * * *

UNITED STATES PATENT AND TRADEMARK OFFICE
CERTIFICATE OF CORRECTION

PATENT NO. : 4,806,532
DATED : February 21, 1989
INVENTOR(S) : Thomas P. Dousa

It is certified that error appears in the above-identified patent and that said Letters Patent is hereby corrected as shown below:

At Col. 1, line 13, for "$na^+_o>]$" read --$Na^+_o > Na^+i]$--.

At Col. 2, line 35, for "photophonof$_o$rmic" read --phosphonof$_o$rmic--.

At Col. 2, line 52, for "with" read --without--.

At Col. 2, line 54, before this line insert --Figure 2 is a graphical depiction of the specificity of--.

At Col. 4, line 4, for "cicyclohexylamine" read --dicyclohexylamine--; for "satls," read --salts,--.

At Col. 4, line 62, for "carries" read --carriers--.

At Col. 5, line 2, for "does" read --dose--.

At Col. 6, line 6, for "pH = t.5," read --pH = 7.5,--.

At Col. 6, line 64, for "220" read --200--.

Signed and Sealed this

Thirtieth Day of January, 1990

Attest:

JEFFREY M. SAMUELS

*Attesting Officer*     *Acting Commissioner of Patents and Trademarks*